United States Patent [19]
Watrous

[11] Patent Number: 5,967,981
[45] Date of Patent: Oct. 19, 1999

[54] TIME SERIES PREDICTION FOR EVENT TRIGGERING

[75] Inventor: Raymond L. Watrous, Belle Mead, N.J.

[73] Assignee: Siemens Corporate Research, Inc., Princeton, N.J.

[21] Appl. No.: 08/938,197

[22] Filed: Sep. 26, 1997

[51] Int. Cl.⁶ ........................................... A61B 5/00
[52] U.S. Cl. .................. 600/428; 600/413; 600/509; 600/521; 128/925; 706/21; 706/924
[58] Field of Search ..................... 600/411, 428, 600/413, 422, 408, 515–519, 509, 521; 128/925; 395/924, 21, 22; 340/601; 73/170.16; 706/21, 20, 924

[56] References Cited

U.S. PATENT DOCUMENTS

| | | | |
|---|---|---|---|
| 5,400,795 | 3/1995 | Murphy et al. ........................... | 128/925 |
| 5,445,162 | 8/1995 | Ives .......................................... | 600/413 |
| 5,490,062 | 2/1996 | Leach et al. .............................. | 364/421 |
| 5,524,631 | 6/1996 | Zahorian et al. ........................ | 128/698 |

OTHER PUBLICATIONS

Williams, "The Weather Book An Easy–To–Understand Guide To The USA's Weather", pp169–183, Apr. 1992.

*Primary Examiner*—Ruth S. Smith
*Attorney, Agent, or Firm*—Lawrence C. Edelman

[57] ABSTRACT

Delays in event detection in time-varying data can be reduced by predicting the time-varying data and then detecting the event in the predicted data. This finds application in the triggering of medical imaging devices, where physiological events can be detected in the time-varying data. An artificial neural network can be trained to predict data such as ECG signals from which a detection algorithm can accurately predict the occurrence of an event that will serve as a reference point for triggering.

5 Claims, 2 Drawing Sheets

TIME SERIES PREDICTION FOR EVENT TRIGGERING

BACKGROUND OF THE INVENTION

Certain physical phenomena can be characterized by time-varying relationships, some of which may contain repetitive features. On occasion, one may wish to perform an act at a specific point in time, perhaps upon the occurrence of a particular feature. One particular application for this lies in medical imaging.

In imaging applications such as magnetic resonance imaging (MRI), computerized tomographic (CT) scanning, ultrasound, and positron emission tomography (PET), a series of related images should ideally be taken at the point where the heart (or other anatomy of interest) is in a relatively constant posture. This condition can be assured by synchronizing the imaging with a fixed point or phase in the heartbeat cycle. For example, the electrocardiogram (ECG) signal, specifically the R-wave within the QRS event in the ECG signal provides such a reference point, as it occurs when the ventricles are contracted.

Known methods for detecting the occurrence of an event often suffer from a processing delay. By the time such methods indicate that an event has occurred, that event has passed, and the anatomy may have undergone a significant change in position or posture. Preferably, the trigger should immediately follow the occurrence of the event. By predicting the signal some interval of time in advance of when the event will occur, one can compensate for the delay in the event detection process.

DESCRIPTION OF THE INVENTION

Figure 1:
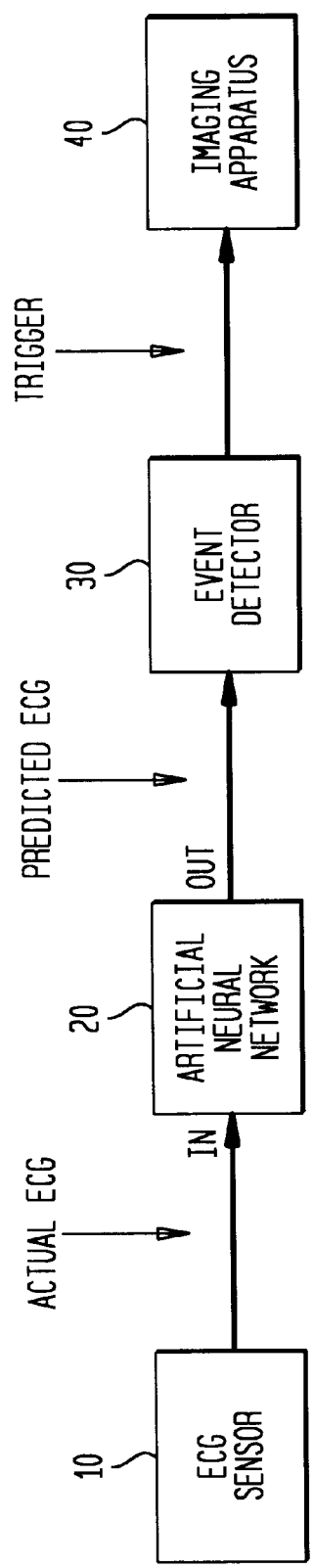
FIG. 1 is a block diagram of an apparatus for triggering an imaging device.

An imaging apparatus can be triggered in an accurate and timely fashion with the arrangement shown in FIG. 1. In the following example, the R-wave from an ECG signal is used to trigger an imaging device. However, it should be understood that this technique and apparatus are not limited to ECG signals, or medical imaging for that matter.

An ECG sensor 10 obtains actual ECG data from the patient and provides a signal in an appropriate format to an artificial neural network (ANN) 20. Given sufficient data, the ANN undergoes a learning or training process, ultimately achieving the capability of generating predicted ECG data that accurately tracks the actual ECG data of the patient.

An event detector 30 receives the predicted ECG data and detects the QRS event and specifically the R-wave component. Alternatively, another feature of the ECG data could be detected. In response to the detection of the QRS event or some other feature, the event detector 30 sends a trigger signal to the imaging apparatus 40.

The ECG sensor 10 can be any device that will monitor the patient and provide an ECG signal. Such devices are well known in the art.

The artificial neural network 20 is selected to provide the degree of resolution necessary to model the ECG data, a non-linear signal. The parameters that may be considered include the sampling rate, the number of samples, and the prediction period. The number of samples determines in part the number of units in the hidden layers of the neural network. Ten samples at a sample rate of 200 Hz have been found to provide satisfactory information for the purposes of an accurate prediction but other sample sizes may be employed as suits the application.

Figure 2:
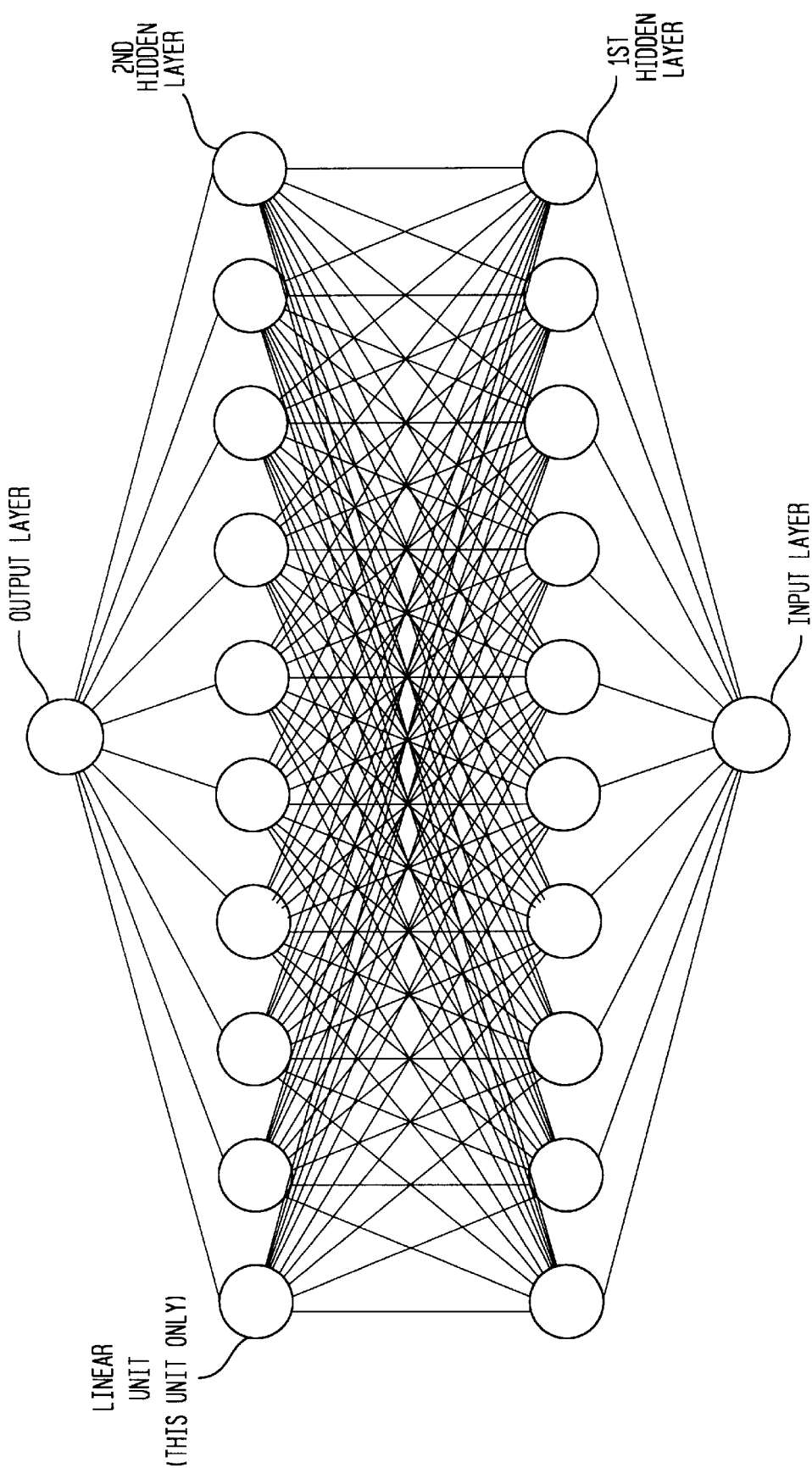
FIG. 2 is diagram of a neural network that may be used with the apparatus of FIG. 1.

In one configuration, the ANN 20 has input and output layers and at least two hidden layers having assigned weights. Since the ECG signal is one dimensional, the input and output layers each consist of a single unit. Based on a sample size of ten, the first hidden layer has ten linear units, representing ten time-lagged input values, having fixed weights of unity and successively increasing delay parameters. The second layer consists of non-linear units except for one linear unit fully connected to the first hidden layer to account for linear predictive elements in the signal. Initially, weights of small values are randomly assigned to the non-linear units and then modified as the network 20 learns. Finally, the ANN 20 may have a threshold unit that receives no inputs but provides a constant-output offset of unity to each of the noon-linear units in the second layer and the output unit. A diagram of the ANN 20 described here is shown in FIG. 2. In lieu of this particular topology, the neural network could have either one, or three or more hidden layers and a different number of units, as is well understood in the design of such models.

As the ANN 20 receives ECG data, it adjusts the weights on the second hidden layer until convergence is achieved. At that point, the ANN 20 is producing an accurate prediction of the ECG data. The predicted ECG signal is updated over time and the ANN 20 may optionally continue "learning" during subsequent imaging.

The ANN 20 can be trained using methods discussed in Watrous, Raymond L., "Learning Algorithms for Connectionist Networks: Applied Gradient Methods for Nonlinear Optimization," *First International Conference on Neural Networks*, San Diego, Calif., June 1987, vol. II, pp. 619–27; and Wasserman, Philip D., *Advance Methods in Neural Computing*, New York: Van Nostrand Rheinhold, 1993, incorporated herein by reference.

The event detector 30 detects an event in the ECG signal, such as the R-wave in the QRS event. Since the there is some finite delay due to processing by the event detector 30, ideally the ANN 20 should provide an accurate prediction of the ECG data for at least a significant portion of the delay experienced in the event detector 30. Methods of detecting events such as the QRS event are disclosed in U.S. Pat. No. 4,934,376, issued Jun. 19, 1990, to Armington, for a Method and Apparatus for Detecting Heartbeats, and U.S. Pat. No. 5,381,803, issued Jan. 15, 1995, to Herleikson et al., for a QRS Detector for Defibrillator/Monitor, incorporated herein by reference.

As noted above, the method of predicting a time-varying signal and then acting upon the prediction has wide application wherever there is a delay in a subsequent process. In addition to triggering an imaging device, it could be used to trigger a defibrillator, a mechanism for pharmaceutical delivery, or some other medical device. The data upon which the device acts is not limited to ECG signals; the data can include a phono cardiogram, an arterial pulse signal, or another time-varying signal. The model for predicting can utilize linear or non-linear artificial neural networks, or a time-series predictive method such as time-series prediction algorithms including auto-regressive algorithms and auto regressive moving average (ARMA) algorithms.

Figure 3:
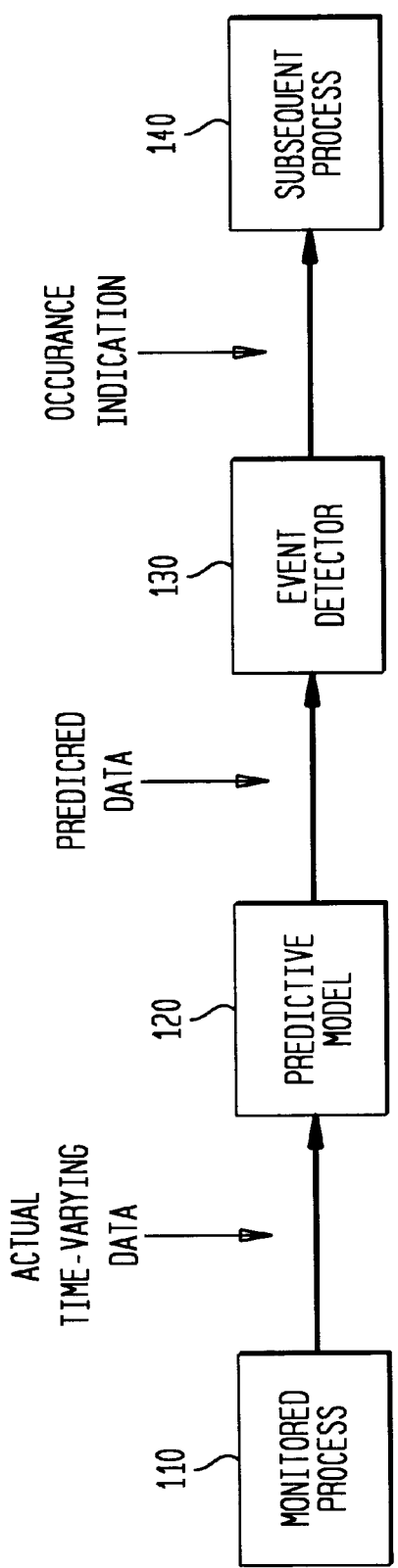
FIG. 3 is a block diagram of an apparatus for predicting time-varying data and detecting an event within the data.

A generalized arrangement of the apparatus is illustrated in FIG. 3. There, a monitored process 10 provides actual time-varying data to a predictive model 120. The model 120 generates predicted data in real time from which an event detector 130 detects the occurrence of an event. A subsequent process 140 utilizes the event indication as required.

What is claimed is:

1. An apparatus, comprising:

means for sampling actual time-varying data;

means, responsive to the means for sampling actual time-varying data, for predicting the data;

means for detecting the occurrence of a QRS event in the predicted data and providing an indication of the occurrence.

2. An apparatus for triggering a medical imaging device, comprising:

means for sampling actual ECG data;

an artificial neural network model, responsive to the actual ECG data, for predicting ECG data;

means for detecting the occurrence of an event in the predicted ECG data;

means, responsive to the means for detecting the occurrence of an event, for triggering the imaging device; and means for continually updating the model.

3. A method, comprising the steps of:

predicting ECG data with an artificial neural network model or a time-series prediction algorithm trained on actual ECG data;

detecting the occurrence of a QRS event in the predicted ECG data; and triggering an imaging device in response to the detected event.

4. A method, comprising the steps of:

sampling actual time-varying data;

in response to the actual sampled data, predicting the data;

detecting the occurrence of a QRS event in the predicted data; and providing an indication of the occurrence.

5. A method, comprising the steps of:

sampling ECG data;

providing the ECG data to an artificial neural network model;

training the artificial neural network model to predict ECG data;

generating predicted ECG data with the artificial neural network model;

detecting the occurrence of a QRS event in the predicted ECG data;

triggering an imaging device in response to the detected event; and updating the model.

* * * * *